(12) United States Patent
Breen

(10) Patent No.: US 11,388,888 B2
(45) Date of Patent: Jul. 19, 2022

(54) CULTURED QUAHOG PEARLS AND METHODS OF PREPARATION THEREFOR

(71) Applicant: Mercenaria LLC, Duxbury, MA (US)

(72) Inventor: Brendan Michael Breen, Duxbury, MA (US)

(*) Notice: Subject to any disclaimer, the term of this patent is extended or adjusted under 35 U.S.C. 154(b) by 196 days.

(21) Appl. No.: 16/506,400

(22) Filed: Jul. 9, 2019

(65) Prior Publication Data

US 2020/0015459 A1 Jan. 16, 2020

Related U.S. Application Data

(60) Provisional application No. 62/696,038, filed on Jul. 10, 2018.

(51) Int. Cl.
*A01K 61/56* (2017.01)
*A01K 67/033* (2006.01)

(52) U.S. Cl.
CPC .......... *A01K 61/56* (2017.01); *A01K 67/0334* (2013.01)

(58) Field of Classification Search
CPC ........ A01K 61/54; A01K 61/56; A01K 61/57; A01K 61/00; A01K 61/51; A01K 2217/05; A01K 67/0334
See application file for complete search history.

(56) References Cited

U.S. PATENT DOCUMENTS

| 3,871,333 A * | 3/1975 | Gotoh ............... A01K 61/54 119/244 |
| 5,347,951 A | 9/1994 | Fankboner |
| 2007/0193526 A1* | 8/2007 | Batzer ............... A01K 61/54 119/244 |

OTHER PUBLICATIONS

Awaji and Machii, "Fundamental Studies on In Vivo and In Vitro Pearl Formation-Contribution of Outer Epithelial Cells of Pearl Oyster Mantle and Pearl Sacs", Aqua-BioScience Monographs, vol. 4, No. 1, pp. 1-39, Sep. 16, 2011 [retrieved on Jun. 8, 2021], (Year: 2011).*
Pearl-Guide.com, I want to learn how to implant a nucleus in a clam, [retrieved on Jun. 8, 2021], Retrieved from internet: https://www.pearl-guide.com/forum/pearls/consumer-q-a/2208-i-want-to-learn-how-to-implant-a-nucleus-in-a-clam/page2. pp. 1-4 (Year: 2008).*
Erin L. McGinty et al., "Diagnostic genetic markers unravel the interplay between host and donor oyster contribution in cultured pearl formation", Aquaculture,[retrieved on Jun. 8, 2021]. Retrieved from internet: https://www.sciencedirect.com/science/article/pii/S0044848611001402?via%3Dihub (Year: 2011).*

(Continued)

*Primary Examiner* — Monica L Barlow
(74) *Attorney, Agent, or Firm* — Carol A. Marmo; Eckert Seamans Cherin & Mellott, LLC

(57) ABSTRACT

The invention relates to a cultured bivalve mollusk (particularly quahog) pearl and a method of preparation thereof. The method includes implanting a nucleus material and a donor bivalve mollusk mantle tissue in the gonad or gut area of an anesthetized bivalve mollusk. An ideal bivalve mollusk or a quahog is four-years old or younger for rapid pearl production. The cultured pearl is harvested after a period ranging from six months to three years. Such cultured bivalve mollusk pearl is identical in appearance to the natural pearls.

7 Claims, 4 Drawing Sheets

(56) References Cited

OTHER PUBLICATIONS

Blay et al., "Optimal age of the donor graft tissue in relation to cultured pearl phenotypes in the mollusc, Pinctada margaritifera". [retrieved on Jun. 8, 2021]. Retrieved from internet: https://journals.plos.org/plosone/article?id=10.1371/journal.pone.0198505 (Year: 2018).*

International Search Report and Written Opinion for PCT/US2019/040999, dated Sep. 30, 2019.

Awaji and Machii, "Fundamental Studies on In Vivo and In Vitro Pearl Formation—Contribution of Outer Epithelial Cells of Pearl Oyster Mantle and Pearl Sacs", Aqua-BioScience Monographs, vol. 4, No. 1, pp. 1-39, Sep. 16, 2011.

pearl guide.com, "I Want to Learn How to Implant a Nucleus in a Clam", Jan. 10, 2008, [retrieved on Sep. 6, 2019]. Retrieved from Internet: <URL: https:www.pearl-guide.com/forum/showthread.php72139-I-want-to-learn-how-to-implant-a-nucleus-in-a-clam/page4> Entire Document.

* cited by examiner

_US 11,388,888 B2_

CULTURED QUAHOG PEARLS AND METHODS OF PREPARATION THEREFOR

CROSS-REFERENCE TO RELATED APPLICATIONS

This application claims priority to U.S. Provisional Patent Application No. 62/696,038, entitled "CULTURED QUAHOG PEARLS AND METHODS OF PREPARATION THEREFOR", filed Jul. 10, 2018, the contents of which are incorporated herein by reference in their entirety.

BACKGROUND OF THE INVENTION

Field of the Invention

The present invention relates to cultured bivalve mollusk pearls and preparation thereof, which includes unique methods of nucleation designed in accordance with the anatomy and composition of the bivalve mollusk. Of particular importance are cultured quahog (_Mercenaria mercenaria_) pearls.

Description of Prior Art

Almost all species of shelled mollusks are capable of producing some kind of pearls, typically occurring in the mantle folds. Pearls are formed as a preventative measure against a foreign object (microorganism, piece of sand, shell, etc.) entering the body of the mollusk, and becoming lodged in the soft tissue in some fashion. This "irritant" is then surrounded in pearl material as a means of sequestering off the foreign object, so in the event it cannot be expelled, its presence can no longer infect, disturb, or hurt the mollusk. The mollusk's mantle (protective membrane used for transportation of solids and food) deposits calcium carbonate ($CaCO_3$) in the form of the mineral aragonite or a mixture of aragonite and calcite. Nacreous pearls are mainly composed of Calcium Carbonate crystals, while non-nacreous pearls such as the quahog pearl are generally composed of Calcite and Aragonite crystals. Pearls that occur spontaneously in the wild are referred to as natural pearls. Cultured or farmed pearls are formed inside a living mollusk using human intervention as well as natural processes. Both wild and cultured pearls are formed by the same natural process with the same crystalline composition beyond the irritant, with the only difference being a cultured pearl has intentionally triggered it, given the deliberate act of nucleation.

In the case of a cultured pearl, the nucleation is done in a fashion in which an "irritant" i.e. a nuclei bead is intentionally implanted into the mollusk in a desired area to trigger pearl production around itself. The pearl material that is deposited around a cultured pearl is of the same molecular makeup, with the only difference being in the events that led up to pearl production occurring, i.e. how the irritant got there, with a wild pearl being done by chance, and a cultured pearl being done so in a deliberate fashion. Both pearls are composed exactly the same beyond the irritant that caused pearl production, and visually appear identical.

The quahog (the genus _Mercenaria mercenaria_) is a Mollusca/Bivalvia/Heterodonta/Venerida by classification. The quahog is a hard, round clam or hard-shell clam that is an edible marine bivalve mollusk. The quahog is native to North America. The quahog pearl is a rare non-nacreous pearl. The pearl of the quahog is composed of mainly aragonite or a mixture of aragonite and calcite in minute crystalline form.

The mollusk creates a pearl sac to seal off the irritation. When a nucleus is surgically implanted in the mollusk's flesh, the mollusk recognizes it as an irritant and begins to coat it with calcium carbonate. Cultured pearls are the response of the mollusk to the implantation of a foreign object, often accompanied by, or done solely with a piece of mantle tissue. A tiny piece of mantle tissue (called a graft) from a donor mollusk is generally transplanted into a recipient gonad, causing a pearl sac to form into which the tissue precipitates calcium carbonate. There are a number of methods for producing cultured pearls using freshwater or saltwater mollusks, which include transplanting the graft into the mantle or into the gonad, and adding a spherical, or otherwise shaped bead as a nucleus.

Bivalve mollusks grow throughout their entire life cycle along an asymptotic curve. As they get larger in size, their rate of growth slows and then level off. Generally, using quahogs as an example, the most rapid growth occurs between 0 and 3 years, while the quahog is from "Petite" to "Topneck" size. The size grading of quahog clams are as follows given ideal conditions. It should be noted that regionality plays some role in size grading, which can lead to some variation. Below is a widely accepted means of grading in a commercial/Scientific setting:

Seed/Juvenile (0-6 months, width of <1 inch)
Petites/Pastas (6 months-1.5 years, width of 1-1.5 inches)
Littleneck (1-2.5 years, width of 1.5-2 inches)
Midneck (2.5-3 years, width of 2-2.5 inches)
Topneck (2.5-4 years, width of 2.5-3 inches)
Cherrystone (3.5+ years, width of 3-4 inches)
Chowder/Quahog/Hogs (4+ years, width of 4+ inches)

The bivalve mollusks in the current invention roughly follow the same growth rate as quahog.

BRIEF SUMMARY OF THE INVENTION

In accordance with the present invention, methods have been developed to form cultured bivalve mollusk pearls as a result of nucleation designed in accordance with the anatomy and composition of the bivalve mollusk.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF PREFERRED EMBODIMENTS

Figure 1:
FIG. 1 is a photograph of an open quahog selected as a donor.

The present invention relates to cultured bivalve mollusk pearls and methods for forming them using human intervention. As aforementioned, the methods provide unique nucleation designed in accordance with the anatomy and composition of the bivalve mollusk.

Growth, and thus shell production, occurs most rapidly in the smaller sizes of bivalve mollusks with the growth curve flattening out at the larger sizes. Using quahogs as an example, growth is leveled off at the Cherrystone/Chowder stage. Pearl production in terms of volume correlates closely with shell production, given the similarities in molecular structure between a shell and a pearl. This being said, in order to achieve the quickest/most efficient rate of pearl production, it is beneficial to nucleate the quahog at the smallest size possible.

On the other hand, it is also beneficial to nucleate quahogs utilizing the largest nuclei bead possible, as the larger the bead the more rapidly the quahog can achieve a larger size, as less pearl material deposition is needed to do so. Although a 5 mm bead, for example, is generally too large to be nucleated into a small quahog such as a petite without causing a high rate of mortalities due to the relative stress the mass of this bead causes upon implantation. So for peak pearl production, and a sizable nuclei bead, a middle ground must be sought in most cases. Generally quahogs no older than 4 years in age are the ideal candidates for nucleation, i.e., little neck quahogs (1-2.5 yrs), smaller tops (<3 yrs), and small cherrystones (3.5 yrs).

As described herein, the methods and techniques utilized to create the pearls are suitable for the morphological characteristics of the quahog ("hard clam"), although it is understood and contemplated that these methods and techniques can be implemented in any bivalve mollusk, bivalve mollusk Heterodonta, or bivalve mollusk Heterodonta Venerida. Examples include but are not limited to *Nuttallia obscurata, Pitar dione, Austrovenus stutchburyi, Dosinia anus, Spisula solidissima* and the like.

The composition of the pearls produced according to the invention is predominately composed of aragonite and calcite crystals (e.g., "non-nacreous pearls"). The term "nacreous" describes how a calcium carbonate crystalline structure is laid down as shell material. For nacreous layers (in shells that have them) the crystal formation is sheet-like, and the crystals are laid down in over-lapping fashion (e.g., roof shingles). The iridescence of nacreous pearls comes from the refraction of light through layers of the crystals of varying thickness. Non-nacreous pearls can be predominately of aragonitic (aragonite) crystals or calcitic (calcite) crystals. Light is refracted differently within non-nacreous pearls (e.g., quahog pearls), which gives a unique "shimmer" in contrast to an Akoya or South Sea pearl for example. Thus, use of the term "non-nacreous" herein refers to the aragonite/calcite crystalline structure of the pearls according to the invention.

Nuclei and Donor Tissue Nuclei are the implanted "irritant" around which pearls is formed. When a foreign object enters a mollusk that cannot be expelled, the creature's response is to sequester, or block it off in order to quarantine the intruder to prevent infection or damage. The means in which the foreign object is blocked off is through depositing pearl material around it, and that is how a cultured pearl is formed. The nucleus bead is the "foreign object" and its intentional implantation is what triggers the natural defense mechanism of the mollusk to create a pearl. The insertion of the nucleus bead (the irritant) is commonly referred to as nucleation. This can occur on any part of the mollusk in theory, although the gonad is generally preferred due to its fast regenerating tissue; the incision in which the nucleus bead is placed in heals quicker, amongst other reasons. The nucleus bead may be of any size, shape, or origin. Spherical beads derived from shell are typically used. Optionally, beads from a bivalve mollusk, or from the same species as the mollusk for cultured pearl growth is preferred. In practice, beads such as those milled from freshwater mussel shells or from quahog may be used.

The donor tissue is derived from the mantle of the mollusk due to the fact that shell creation occurs outward from the mantle tissue. The donor mollusk may be of a different species, although of the same species is preferred. In most embodiments, a 3 mm×3 mm section of mantle tissue is selected. A pearl's structure is very similar to that of the shell of the mollusk, so in using donor tissue from the mantle and placing it next to the nucleus bead, a high concentration of pearl-producing cells is placed next to the nucleus bead. The donor mantle tissue and the nucleus bead allow for more rapid pearl production. This donor tissue piece is generally taken from the edge of the mantle, as new shell production occurs from the edge of the mantle, thus a section of mantle exhibiting the highest rate of shell (and inevitably pearl) production is used.

Although a pearl can be formed regardless of where the implantation occurs in a mollusk in most circumstances, the extra donor mantle tissue next to the nucleus bead enhances the success and growth rate. Additionally, the mantle tissue that is placed next to the nucleus bead is accepted by the mollusk, and the donor mantle tissue (full of pearl producing cells) is grown around the nucleus bead, in order to initiate more rapid pearl production. Essentially, the mollusk realizes it needs to sequester off a foreign object (the nucleus bead), and identifies that there is a portion of mantle tissue (the donor tissue) which is rich in pearl-producing cells conveniently located right next to the nucleus bead. So the mollusk accepts the donor tissue, and grows the pearl around the bead.

Optionally, in order to obtain the highly prized purple pearl coloration, the top shell of a quahog possessing a high percentage of purple (wampum) on its shell is selected as a donor for pieces of mantle tissue. Typically, the donor tissue is used for nucleation immediately after harvesting.

Figure 2:
FIG. 2 is a photograph of showing a piece of mantle tissue being cut from the shell.

FIG. 1 is an open quahog top shell selected as a donor. FIG. 2 shows a piece of mantle tissue being cut from a location directly in contact with the most intense purple area of the shell. This portion of the mantle tissue is preferably used as the donor tissue in nucleation. Typically, the donor tissue is around 3 mm×3 mm in size.

As discussed above, the size, shape and composition of the nucleus bead can vary, as well as the size and shape of the mantle tissue. In certain embodiments, a 5 mm diameter nucleus bead and a 3 mm×3 mm segment of mantle tissue is used. The size of each is limited by the size of the incision and the size of the mollusk. Larger beads and the donor mantle promote quicker pearl growth but cause greater trauma to the recipient mollusk. Milling of the shell may be necessary to prepare a nuclei bead of an appropriate size. Although the shape of the nucleus bead is not particularly limited, a spherical or near spherical shape is preferred because spherical pearls are prized.

Figure 3:
FIG. 3 is a photograph of an unmilled section of quahog shell (left) next to a milled bead (right)

FIG. 3 shows an unmilled section of quahog shell (left) next to a milled bead (right). Generally, shell segments possessing purple coloration ("Wampum") are used. The benefit of this is unique to the quahog, as a purple crystalline structure composed of Aragonite and Calcite will bind better to a respective piece of a quahog shell with similar coloration and molecular composition.

Nucleation

A mollusk for use in the method of the invention can be harvested wild or from an aqua-culture operation. Preferably, mollusks (or quahogs) 4-years old or younger are used for the invented method. More preferably, 3-years old or younger, 2-years old or younger, or 1.5-years older or younger. Size may be used as an alternative selection measure. The preferred size of mollusks (or quahogs) for optimal pearl production is 3.5 inches or less in width. More preferred size is 3 inches or less, 2.5 inches or less, 2 inches or less, or 1.5 inches or less in width. The mollusk may be placed in an indoor seawater system for an adjustment period. The period of adjustment varies, and may be about one week. The mollusk is then anesthetized using conventional methods. For example, the mollusk can be transferred from the seawater system to a solution bath that includes a neurotransmitter, such as 2-phenoxyethanol and acetylcholine. The amount of neurotransmitter varies, and may be present in a concentration of about 2.5 ml/L. The mollusk remains in the bath for a period of time that is suitable for anesthetization to occur. A typical anesthetization period may be between 4 and 10 minutes, depending on the size of the mollusks (or quahogs).

In accordance with the invention, an incision (or a cut) is made in the shell of the anesthetized mollusk. The terms "an incision" and "a cut" are herein used interchangeably. The size and shape of the incision varies. In certain embodiments, the incision is made in the shape of a square, and the size ranges from about 1 cm×1 cm to about 2 cm×2 cm. It is preferred to make the incision in a location that provides unobstructed access to the gut, the gonad, or the abductor muscle, while not being near the heart of the mollusk.

Figure 4:
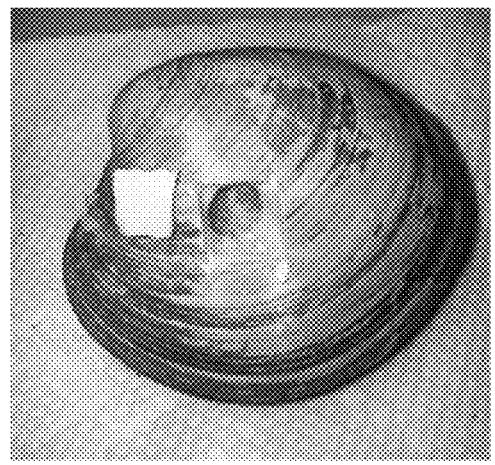
FIG. 4 is a photograph of a piece of shell removed from the cut square in the shell of a quahog, and placed bottom side up next to the cut hole.

The incision made through the shell is done in a certain manner. For example, a circular Dremel tool is used. The shape of the cut is not particularly limited as long as the cut is sized to allow subsequent steps of nucleation. Optionally, incisions are made on four sides of the 1 cm×1 cm square, halfway (50%) through the shell. Next, cuts are made in the center of each side of the square until the shell is almost completely cut through. This cut is done in a manner in which the corners remain attached to the piece of shell to be removed. At this time, a wedge is inserted to the cut into the shell closest to the umbo, and pressure is applied to break the section of shell off. Whatever the shape of the cut, the cuts into the shell are done in a manner in which a thin layer of shell remains behind after the removal of the portion of cut shell, extending beyond the area of the removed piece, covering about at least half of the opening around the periphery, with a small opening in the middle into which the surgical incisions and nucleation are made. This is done to allow the cut portion of the shell a platform to rest on for quicker calcification/healing post nucleation, and as a preventative barrier so materials such as petroleum jelly and epoxy utilized later in the procedure do not enter the cavity of the quahog. FIG. 4 shows a piece of shell removed from the cut square, and placed bottom side up next to the cut hole.

After cutting the shell and removing the portions of the cut shell, an incision is made with a tool, e.g., a scalpel or surgical scissors, suitable to cut through the mantle in order to access the gut or the gonad. The cut through the mantle is made by first poking the scalpel through the mantle tissue, pivoting the scalpel against the mantle tissue, and holding the mantle against the shell for 5-10 seconds. This allows the mantle to remain adhered to the inside of the shell by the action of surface tension. The mantle is thus kept out of the way during the procedure. The technique aids in the healing post-nucleation, as energy does not need to be exerted by the mollusk to recover from repositioning its mantle back into its natural orientation and position. The cut made through the mantle is generally around 5 mm in width to cause as little tissue damage as possible. The incision should be made for an opening wide enough for implantation yet not too extensive to aid recovery. Underneath the mantle, a cut is made into the gut of the mollusk through the muscular tissue, between the two intestinal tracts, and optionally into the gonad. The cut is preferably made at the center where the muscular tissues are thinner. A blunt, round object including but not limited to a blunt pair of tweezers is used to push the gills of the quahog back towards the heart, being mindful not to damage the gills, cause abrasions on the gut, or push the gills so far back that the heart is damaged.

Quahogs are hermaphroditic. As they grow larger, fewer remain male, and more become female, thus losing their gonad. Nucleation can occur in the same manner in quahogs of all sizes. One of the benefits of gonadal nucleation is that it allows for a faster healing process, and thus more rapid pearl production. Gonadal nucleation is preferred likewise for other bivalve mollusks. The inventors have discovered that nucleation in the gonad to be preferred. Cutting above the intestine will result in damage to the stomach of the quahog, and cutting below will occur in the dense muscular tissue of the foot, where it is difficult to successfully nucleate. Cutting to the left or right poses the same problems of damaging other internal organs, and access is additionally not possible without damaging the abductor muscles.

Figure 5:
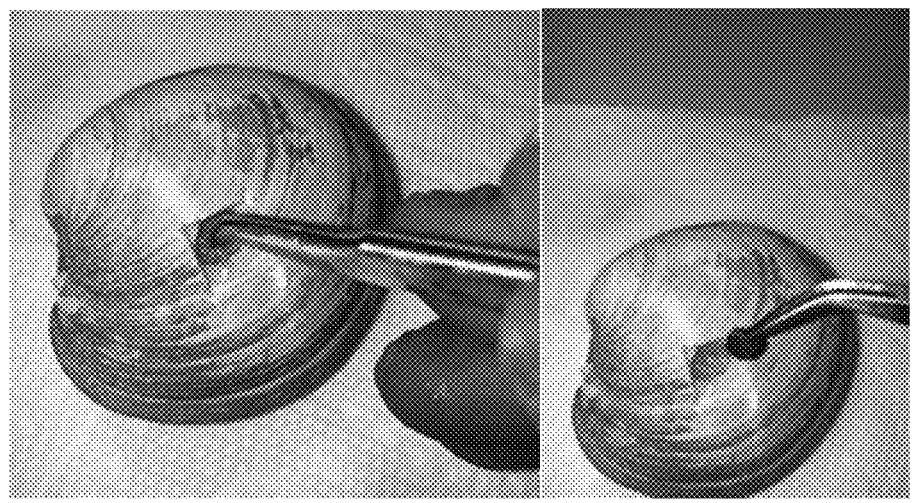
FIG. 5 is a photograph of a piece of mantle tissue (left) and a bead (right) being inserted into the gonad through the incision.

In certain embodiments, during the surgical procedure a majority of the fluid within the mollusk is removed (e.g., with a syringe) and stored to more easily access the gonad. An incision is made in the gonad (e.g., with a scalpel), with care to avoid the intestinal tract. A nucleus bead and a segment of donor mantle tissue are inserted into the incision made in the gut or the gonad. The size, shape and composition of the nucleus bead can vary, as well as the size and shape of the mantle tissue. In certain embodiments, a nucleus bead (5 mm in diameter) and a segment of mantle tissue (3 mm×3 mm) are used. Nucleus beads include those milled from freshwater mussel shells. FIG. 5 shows a piece of donor mantle tissue being inserted into the gonad through the incision (left), followed by a bead (right). The order of insertion is not particularly limited. Typically, the donor mantle tissue and the nuclei bead are placed adjacent to each other in the same pocket created by the incision.

Pieces of shell from the shell cutting process then may be removed. It is not necessary, nor feasible, to remove all fragments of shell. The nucleated mollusks typically expel excess shell fragments within a couple of weeks following the procedure. Such expelling indicates that the mantle is still functioning and moving solids. Thus the mollusk is feeding.

Figure 6:
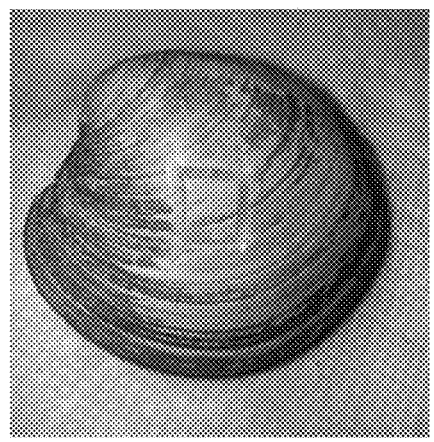
FIG. 6 is a photograph showing the removed section of shell seen in FIG. 4 placed in its original orientation and position, resting on top of the thin section of shell left, with petroleum jelly gently applied within the cracks outlying the cuts around the reapplied shell piece.

If fluid was earlier removed, it then may be re-introduced into the mollusk shell. The piece of removed shell is then placed on top of the hole or opening created earlier. A barrier agent in the form of an ointment or a lubricant, e.g., petroleum jelly, is applied along the edges of the square incision of the shell. The barrier agent is to prevent the later applied sealant from entering into the mollusk by creating a protective barrier that is nontoxic and unharmful to the mollusk. The cut piece of shell is re-applied gently on top of the barrier agent, and a sealant (for example, a marine epoxy resin) is subsequently applied on top of the shell to create a seal. The order of reapplying the cut piece of shell and applying the barrier agent is not particularly limited as long as 1) the cut pieces of shell are returned to their original positions to protect the internal cavity of the nucleated mollusk (or quahog) from external disturbances, and 2) the cracks outlining the cuts around the reapplied shell pieces are filled with the barrier agent. FIG. 6 shows the removed section of shell seen in FIG. 4 placed in its original orientation and position, resting on top of the thin section of shell left intact, with petroleum jelly gently applied within the cracks outlining the cuts around the reapplied shell piece. The shell is wiped clean of the applied barrier agent (petroleum jelly) in order to allow for better adhesion of the sealant. A sealant such as an adhesive/bonding agent or material, including and not limited to a marine epoxy resin, is applied above the returned shell section and petroleum jelly. The sealant serves as an additional protective shield for the internal cavity of the quahog. Petroleum jelly is selected because it is not toxic to the quahog. The application of petroleum jelly and epoxy resin is not limited to any instrument, such as a wooden paint mixer. The barrier agent may not be necessary if a nontoxic or unharmful sealant is used directly to seal off the shell of the mollusk.

The nucleated and sealed mollusk may be optionally wrapped while the sealant is setting. A piece of food wrap or other wrapping material may be used. This is done because post-nucleation, muscle contractions occur within the quahog, which results in pressure being exerted upon the cut segment of shell, both inward and outward. The wrap is applied in a manner in which it is not so tight that the sealant is pressed through the cuts into the clam, but still with enough force that the outward pressure applied from the quahog does not push the piece of shell off. After a period or approx. 1 hour, quahogs will generally comply and stop exerting varying levels of pressure on the cut. The wrapping has the additional benefit of forcefully mitigating contractions, which leads to less stress on the organism, and better nucleus bead retention. The nucleated and sealed mollusk is stored at a temperature that allows the sealant to set and harden. In certain embodiments, the mollusk is stored in a refrigeration unit overnight at a temperature from 37 to 39° F.

Once the sealant is hardened, the mollusk may be returned to an intensive or extensive system until it exhibits digging behavior on its own, which is indicative of successful healing of the mantle and gonad, acceptance of the mantle tissue donor and nuclei, and formation of a pearl sac. This behavior may be observed about 4 and 6 weeks following the procedure. This is useful to demonstrate the healing of the gut incision. Quahogs may also be put right into their respective system (extensive or intensive) right after their procedure, and buried into the substrate with their excurrent siphon pointing up, right below the surface. Nuclei retention is higher in the clams which are placed directly into the mud. Gut healing takes generally 4-6 weeks, and full mantle healing takes 2-5 months depending on the time of year. Full shell calcification around the shell incision generally takes 5-6 months.

Harvest

Figure 7:
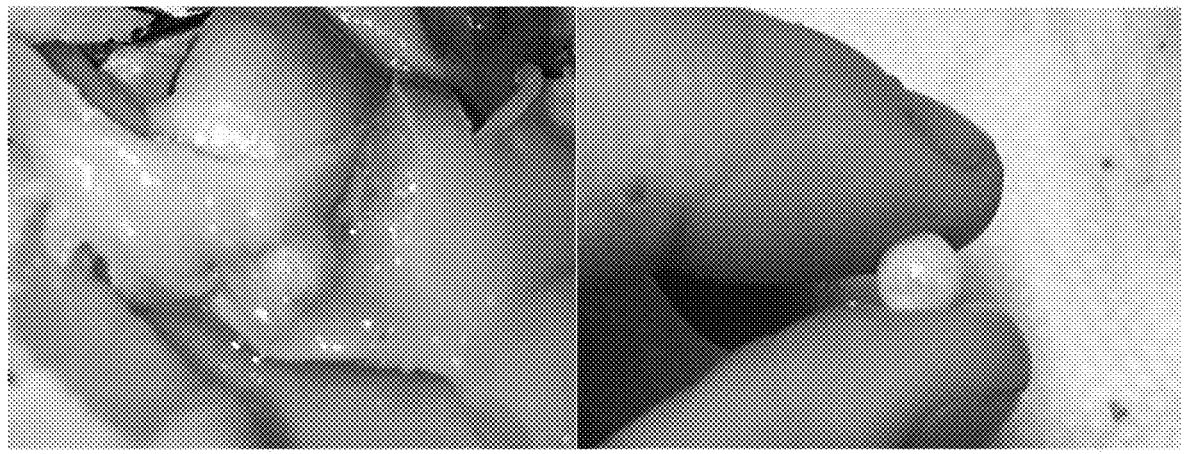
FIG. 7 is a photograph showing a pearl being extracted from the gonad/gut of the quahog (left); and the pearl removed from the gonad with its pearl sac still present (right)

After an appropriate growth period, for example, ranging from 5 months to three years, the pearl is harvested via a surgical procedure. The technique is not particularly limited. As an illustration of harvesting a pearl from the sac, two cuts are made with an appropriate tool (e.g., a dremel tool) along the edge of the shell in order to access and cut the abductor muscles with an appropriate tool (e.g., a scalpel). FIG. 7 (left) shows a pearl being extracted from the gonad/gut of the quahog. The pearl sac appears as a thin membrane surrounding the pearl. This pearl sac was formed from the cells of the donor mantle tissue, and grown around the nucleus bead to allow for maximal pearl production. Once access is achieved, the pearl is removed from the gonad as shown in FIG. 7 (right).

Figure 8:
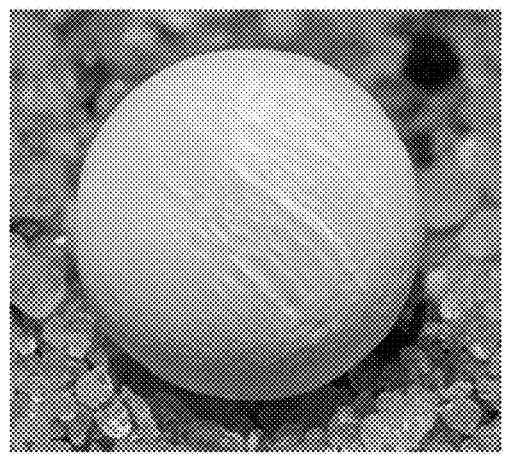
FIG. 8 is a photograph of a cultured quahog pearl according to the method of the current invention.

FIG. 8 is a cultured quahog pearl according to the method of the current invention. This specimen spent 7 months within said quahog, at which point it was extracted for the purpose of data collection. The pictured pearl is spherical (5.44 mm in diameter) and weighs 1.15 carats. This cultured quahog pearl is identical in appearance to the natural quahog pearls.

Method of Preparing Other Pearls

The foregoing method for preparing quahog pearls is applicable to forming pearls in bivalve mollusks other than quahogs. Cultured pearls of bivalve mollusk Heterodonta or bivalve mollusk Heterodonta Venerida may also be raised using the method of invention by adjustments within the skills of the art.

SUMMARY OF INVENTION

The invention provides a method of producing a cultured bivalve mollusk pearl. The method is applicable to cultured pearls of a bivalve mollusk Heterodonta or bivalve mollusk Heterodonta Venerida.

The method includes cutting into the shell to enable effective implantation and nucleation into the gonad, the gut or the abductor muscle of the mollusk for effective pearl growth.

The method involves the following steps:
 a) providing a nuclei bead material;
 b) providing a bivalve mollusk mantle donor tissue;
 c) anesthetizing a bivalve mollusk to afford an anesthetized bivalve mollusk;
 d) creating an opening in a shell of the anesthetized bivalve mollusk;
 e) implanting the nuclei bead material and the bivalve mollusk mantle donor tissue in the anesthetized bivalve mollusk;
 f) allowing growth of the cultured bivalve mollusk pearl for a pre-determined period of time; and
 g) harvesting the cultured bivalve mollusk pearl from the bivalve mollusk.

The method also provides that step e) may comprise the steps of:
 i) cutting through a mantle of the anesthetized bivalve mollusk to allow access to a gonad, a gut, or an abductor muscle;
 ii) placing the nuclei bead material and the bivalve mollusk mantle donor tissue in the anesthetized bivalve mollusk in an area within the gonad, the gut, or the abductor muscle; and
 iii) closing the opening in the shell.

In one embodiment, the bivalve mollusk is a bivalve mollusk Heterodonta, or bivalve mollusk Heterodonta Venerida. In one embodiment, the bivalve mollusk is a quahog.

In one embodiment, the nucleus bead material and the bivalve mollusk donor mantle tissue are implanted adjacent to each other in close proximity in the gonad, the gut, or the abductor muscle. In an optionally embodiment, the placement is in the gonad.

In one embodiment, subsequent to step e) and prior to step f) the method further comprises the step of shielding with a sealant a first area of the shell that is over the opening and a second area of the shell that is surrounding the first area of the shell. Optionally, the sealant is a marine epoxy resin. Optionally, prior to shielding, a barrier layer is created by applying a nontoxic and/or unharmful barrier agent to the cracks in the shell (formed for implanting) to prevent the sealant from contacting the interior cavity of the bivalve mollusk. Optionally, the barrier agent is a petroleum jelly.

In one embodiment, the bivalve mollusk for implantation is 4 years or younger in age, preferably 2.5-years old or younger, more preferably 2-years old or younger, or more preferably 1.5-years older or younger. In one embodiment, the bivalve mollusk is 3.5 inches or less in width, preferably 2.5 inches or less, preferably 2 inches or less, or preferably 1.5 inches or less.

In another embodiment, the bivalve mollusk mantle donor tissue is harvested from a second bivalve mollusk. In another embodiment, the second bivalve mollusk is the same species. In another embodiment, the nuclei bead material is a shell fragment of a mollusk. In another embodiment, the bivalve mollusk mantle donor tissue is 3 mm×3 mm. In another embodiment, the nucleus bead material is 5 mm in width.

In a preferred embodiment, the present invention includes, but is not limited to, the following attributes and characteristics;

The taxonomic originality of a pearl cultured in the venerid bivalve *Mercenaria mercenaria;*
Shell incision;
A single opening in the shell and the mantle for the purpose of direct nucleation in the gonad, the gut, or the abductor muscle;
Precision nucleation through gut muscular tissue, between intestinal tracts, into the gonad of the quahog;
Nucleation utilizing a nuclei bead milled from quahog shell, preferably the area containing the most "Wampum" (purple coloration);
Nucleation without the traditional use of a wire, probe, nut-like device, string, or artificial cover;
Sealing of the shell with the removed piece of the shell, utilizing a sealant such as a marine epoxy resin, and a barrier material in the form of an ointment/lubricant (e.g., petroleum jelly);
Method for pearl culture for an Atlantic Ocean, specifically North American Species;
Absence of sutures;
Low mortality upon the end of one production cycle, including the cutting of the shell around the edge of the mantle and the abductor muscles in order to access the pearl; and
Removal and returning of fluid within the mollusk before and after pearl nucleation.

EXAMPLES

Method of Preparing Quahog Pearls

Quahogs (small cherrystones, 3 inches across, likely 3-4 years in age) were wild harvested and placed in an indoor, ambient, untreated seawater system for an adjustment period of approx. 1 week. The quahogs ready for the nucleation procedure were removed from the system and placed in a 2.5 ml/L solution bath of 2-phenoxyethanol for approximately 4-10 minutes. Anesthetized quahogs were removed from the bath, and a 1 cm×1 cm square incision was made in the shell slightly to the left of the umbo, with the umbo facing to the left. The incision was done in this location in order to achieve the best access to the gonad, and be as far away from the heart as possible. The cut through the shell was done in a manner in which full cuts were made on four sides of the incision. First a cut around the full 1 cm×1 cm area was made, halfway through the shell at all points. From here, cuts were made in the center of each side of the square, so the corners remained intact. The shell was then pried off from the side closest to the umbo utilizing a flat prying devise, leaving a thin layer of shell lining a smaller hole into the mantle, for the purpose of preventing epoxy/ointment/lubricant (e.g., petroleum jelly) from seeping into the cavity of the mollusk. Generally, a ¾ portion of the shell layer was left below the pried off portion of the shell, which served for the aforementioned purpose of keeping out foreign materials.

An incision was then made with a scalpel or surgical scissors to cut through the mantle in order to access the gonad. Typically, the incision was 2-7 mm in diameter, although 3-6 mm was also practical. The incision was made by poking the scalpel through the mantel, turning the scalpel 90 degrees, and holding the mantle against the inside of the shell utilizing the flat edge of the scalpel. This was done so the mantel remained attached to the inside of the shell through the surface tension. The action put less stress/damage on the quahog, and kept the mantle out of the way for nucleation.

In some instances, a syringe was used to remove and store the majority of the liquid within the quahog so the gonad could be accessed. The gills of the quahog were then moved gently out of the way towards the umbo of the quahog with a blunt object to prevent damage to the gills, abrasions on the gut. Care was taken not to reach too far back that the heart was touched. An incision was made in the gonad with a scalpel, being careful to avoid the intestinal tract. (It has been found that the procedure is most easily completed in the springtime, as a high condition index results in an enlarged gonad, proving easier access).

A nucleus bead (3-5 mm in diameter or across) and a segment of mantle tissue (about 3 mm×3 mm) were then inserted into the incision made in the gonad. Although the sequence of insertion is not particularly limited, the bead was usually placed in first followed by the piece of donor tissue adjacent to the bead. The remaining larger fragments of the shell from the cutting were then removed. It was not necessary, nor feasible, to remove every single piece of shell because the nucleated quahogs typically expel excess shell fragments within two weeks. Such expelling is also an indicator of survivability, as it demonstrates that the mantle is functioning and moving solids, thus the quahog is feeding.

In instances when fluid was removed, the fluid was re-introduced into the quahog shell with the syringe. The cut section of shell was placed on top of the thin layer of shell that was left in order to prevent petroleum jelly or epoxy from seeping into the cavity of the mollusk. Petroleum jelly is applied around the edges of the shell piece. A marine epoxy resin was then applied on top of the returned shell portion and the cracks to create a permanent seal. A plastic wrap was then wrapped around the quahog to keep the shell piece covering the cut into the shell in place as the epoxy hardened, as muscular contractions from the quahog created varying level of pressure. Nucleated and sealed clams were often stored in a refrigerator unit overnight at a temperature from 37 to 39° F. in order for the epoxy to set and harden.

Once hardened, the clams were either placed directly into the substrate, with their siphons facing upward, or returned to a flow-through system until they exhibited digging behavior, indicating a successful healing of the mantle and gonad, acceptance of the mantle tissue donor and nuclei, and the formation of a pearl sac. This behavior was observed after 4 and 6 weeks. It was not necessary to keep the clams in the system for this period, but it was useful to provide assurance that the grow-out clams have successfully healed, thus successfully overcoming the stress of nucleation through healing. In the event clams are kept in a flow-through system post-nucleation, they can either be moved into an extensive (outdoor) farm, or kept in said flow-through system for grow-out, if available. Retaining the claims in the flow-through system had the benefit of a controlled, accessible location to observe the behaviors of the clams if possible.

Results from the first batch in the inventor's laboratory showed a 40% survival rate on clams that were anesthetized. The survival would be higher absent of a system failure that was caused by fouling from marcroalgal growth within an inflowing water pump, and resulted in the lowering of dissolved oxygen levels within the tank during a 4-day period. The low dissolved oxygen levels led to increased levels of stress within the system, and thus the mortalities of some of the quahogs.

In subsequent batches, a 90% survival rate after one month of nucleation was observed. The majority of mortalities was attributed to environmental factors outside of the procedure mentioned therein.

The pearl growth period is determined by the following factors. First, the desired dimensions of the pearl. Second, the specific deposition rate under the specific ecological environment. A typical period of six months to three years is contemplated by the current invention.

To harvest the pearl, two cuts were made with a dremel tool along the edge of the shell to access and cut the abductor muscles with a scalpel. Once open, pearls were removed from the gonad. All clams experienced mortality upon the harvesting of the pearl. Aside from the nacre deposited on the pearl, further evidence of the success of the inventive method can be seen in the calcification around the incision point of the shell, around which blister pearls ranging from white to gold in color are formed. Pearl sacs from the harvested pearls can be filled with a new nucleus, and re-nucleated in a new quahog if desired.

Data and Notes Obtained in Preparing the Quahog Pearls

March 31

6 quahogs were harvested on March 11, placed in system March 24.

12 quahogs were harvested on March 24, put in system on March 25.

12 quahogs were harvested on March 28; not put in system; used in March 31 experiment.

$1^{st}$ Anesthetic:

45 ml of 2-phenooxyethanol for 3 L of water.

Did not appear to be completely soluble with salt water.

Starting with two of group 2 for 5 minutes.

Post op still alive keeps "clapping".

Does not appear to have damaged quahogs, but may be difficult to tell whether or not it was effective until the same procedure is run on about 100 anesthetized and non-anesthetized clams.

April 1

Clam #1 survived the night. Epoxy hardened, and put into system. In order to get the neurotransmitter right, I need time. The cut open method is fairly time efficient, so I think I will try to crank them out that way. It seems it takes approximately 15 minutes to do one, with most of that time being cutting into the shell. Half anesthetized, half not. Anesthesized ones facing backwards, non-facing forwards.

Got 7 done today, entered all 7 into the system on April 2. 6 of them appeared fine, with one gaping, likely not doing well. Should be noted the day 1 quahog had not burrowed yet. On at least 3 of the procedures, I cut into the gut and saw digested food. I implanted the pearl anyways, whether formation will occur here, or it will be lethal is my question. It is difficult to locate the gonad, especially with the low condition index, very little milt can be seen. I know for a fact a couple of the clams I have prepared thus far did in fact have the bead implanted into their gonad. I think looking from above, the gonad is slightly to the left, closer to the middle. Some ideas on how to reach the gonad and not damage the mantle/labial palps: remove a big section of shell, and instead of cutting the mantle, gently push it out of the way. Remove a piece of the shell off to the left, and come in at a side angle. I would be surprised if there are zero mortalities, once one dies I want to do a careful analysis of what my implantation looks like; how close I am to the marker.

Dremel tool has a poor battery life, only lasts about 4 clams on a full charge; surprised at how long it takes to cut through the shell. Suppose this is due to the fact that it is the smallest one; need to obtain a larger dremel with more output.

April 4

Within 2 days, clams are all filtering, and interesting to note they have expelled lots of/all of the fragments from the incisions to their shells. What this says to me is their mantels are working. They are able to transport solids over their mantles, so they must be able to do the same with food as well id imagine.

At day 17, one mortality. Not surprised, for whatever reason this clam was opening and closing a lot, plus having a hard time staying closed from the get-go. April $17^{th}$—it was moribund so I am doing an autopsy. Nobody has dug into mud.

Locating the gonad can be difficult. Best bet is horizontal incisions with the umbo pointing to the left . . . and hope it splits the difference between the intestinal tracts. Just did one I think worked perfect, was an aggressive procedure but placement was good. I marked its shell by the lip. The other 4, not sure.

April 26

3 more mortalities, after like 10 days in the system. BUT . . . 2 of the three beads have nacre on them. On is actually very noticeable, with another patchier "one". Proof that the method can work.

May 1

6 mortalities, appears as if some must have died on Friday, as they were very dead. So, after 16 days these ones died, interesting to note of the first batch I did, only one mortality since the first one . . . I believe every single one from the second batch died minus one . . . some of the beads have nacre on them too which is great but all these mortalities are worth noting I am fairly positive it was because I did not remove the mortalities as it was the weekend, and the dead one's contract so much bacteria and make ammonia, making the system toxic. The initial mortalities occurred beyond reasonable doubt due to macroalgal growth within the system over the course of the weekend, which lowered Dissolved Oxygen levels to critical levels. I moved the 7 survivors to the opposite tank, hoping that will be ok for them. On the plus side, those 6 look healthy.

May 5

One expelled an extra bead that had been lost below the mantel during the procedure, and it still had some nacre on it. This shows me that the beads must be implanted, as they will expel whatever is freely floating in their body. I only have 7 left, but they look really good. Far less mucus production has me thinking they are healing up nicely. One has been moving around a bit, but nobody has burrowed yet. I might leave these 7 alone in a low stress setting, and fill the other tank, expecting some mortalities.

June 1-September 1

3 mortalities during the summer due to algal blooms, all exhibited signs of nacre production on their nuclei beads.

September 1-December 12

Two more mortalities in late November due to fouling in the system. It is important to note that over half of the mortalities would not have occurred in a more sophisticated system under closer supervision.

Dec. 12, 2017

I harvest my last two quahogs, due to the fact that I am leaving Rhode Island for 5 weeks, and do not want to leave my pearl-bearing mollusks unattended. The results are fantastic on this specimen. 7 months has produced a pearl that is undeniable surrounded in the calcite aragonite crystalline structure that constitutes for quahog nacre. I have this pearl locked in a safe, and it will serve as an example of the success of my method. I call it, "The *Mercenaria* Pearl", dubbed from the Latin name for the quahog, "*Mercenaria mercenaria.*"

The system and method above would yield pearls in a similar or different composition for all shell bearing mollusks in an appropriate environment.

What is claimed is:

1. A method of producing a cultured quahog non-nacreous pearl, comprising the steps of:
   a) providing a nucleus bead material;
   b) providing a quahog mantle donor tissue;
   c) anesthetizing a quahog to provide an anesthetized quahog;
   d) creating an opening in a shell of the anesthetized quahog, comprising:
      cutting through a mantle; and
      making an incision between a gap in the intestinal tract to provide access to a gonad of the anesthetized quahog;
   e) implanting the nucleus bead material and the quahog mantle donor tissue through the incision in an area within the gonad in the anesthetized quahog;
   f) allowing growth of the cultured quahog non-nacreous pearl for a pre-determined period of time; and
   g) harvesting the cultured quahog non-nacreous pearl from the quahog.

2. The method of claim 1, wherein the quahog is 3.5 years or younger in age, or 3.5 inches or less in width.

3. The method of claim 1, wherein the quahog mantle donor tissue is harvested from a second quahog.

4. The method of claim 1, wherein the nuclei bead material is a shell fragment of a second quahog.

5. The method of claim 1, further comprising subsequent to step e) and prior to step f) a step of: shielding with a sealant a first area of the shell that is over the opening and a second area of the shell that is surrounding the first area of the shell.

6. The method of claim 1, wherein the pre-determined period of time is from 6 months to 3 years.

7. The method of claim 1, wherein the nucleus bead material in step e) is wrapped in a pearl sac.

* * * * *